United States Patent [19]
Flynn

[11] Patent Number: 4,506,374
[45] Date of Patent: Mar. 19, 1985

[54] HYBRID COLLIMATOR

[75] Inventor: Michael J. Flynn, Gregory, Mich.

[73] Assignee: Technicare Corporation, Solon, Ohio

[21] Appl. No.: 366,791

[22] Filed: Apr. 8, 1982

[51] Int. Cl.³ ............................................. G03B 41/16
[52] U.S. Cl. .................................. 378/2; 250/363 S; 250/505.1; 378/149
[58] Field of Search .......................... 378/2, 147, 149; 250/363 S, 505.1

[56] References Cited

U.S. PATENT DOCUMENTS

| | | |
|---|---|---|
| 2,688,095 | 8/1954 | Andrews . |
| 2,730,566 | 1/1956 | Bartow et al. . |
| 3,585,387 | 6/1971 | Bramlet . |
| 3,783,282 | 1/1974 | Hoppenstein . |
| 3,961,191 | 6/1976 | Stoner et al. . |
| 4,012,636 | 3/1977 | Engdahl et al. . |
| 4,017,730 | 4/1977 | Barrett . |
| 4,075,483 | 2/1978 | Tancrell et al. . |
| 4,092,540 | 5/1978 | Barrett . |

OTHER PUBLICATIONS

"Digital Tomographic Imaging with Time-Modulated Pseudorandom Coded Aperture and Anger Camera", Koral, et al., *Journal of Nuclear Medicine*, Oct. 26, 1974.
"Coded-Aperture Imaging of the Heart", Rogers, et al., J. Nucl. Med. 21:371-378, 1980.
"Fourier Multiaperture Emission Tomography (FMET)", Renaud, et al., J. Nucl. Med. 20:986-991, 1979.
"A Class of Near-Perfect Coded Apertures", Cannon, et al., IEEE Transactions on Nuclear Science, vol. NS-25, No. 1, Feb. 1978.
"Introducing SPRINT: A Single Photon Ring System for Emission Tomography", Williams, et al., The University of Michigan.

*Primary Examiner*—Craig E. Church
*Attorney, Agent, or Firm*—Audley A. Ciamporcero, Jr.; Michael A. Kaufman

[57] ABSTRACT

A hybrid collimator for tomographic imaging with a scintillation camera comprising a coded aperture plate and a parallel plate collimator. The code plate includes a plurality of lateral slits each of which is radiopaque or radiotransparent pursuant to a time modulated code. The parallel plates define a plurality of radiotransparent channels whose lengthwise orientation is orthogonal to the lateral slits of the code plate. In a preferred embodiment, the code plate is advanced across the channels of the collimator in a direction parallel to their lengthwise orientation rendering a time coded pattern that is identical for each channel.

5 Claims, 11 Drawing Figures

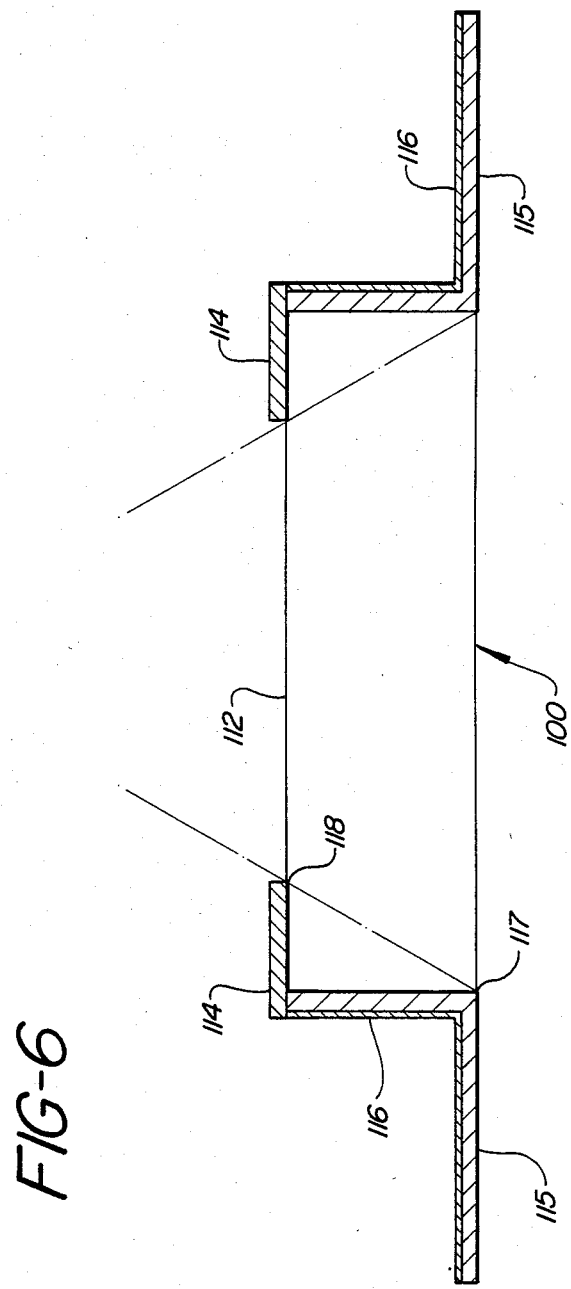

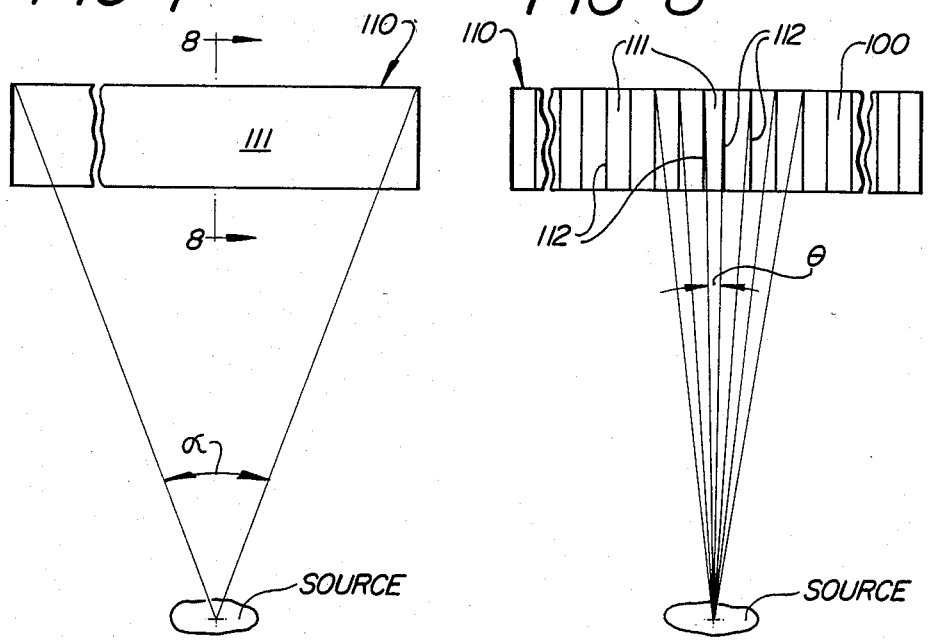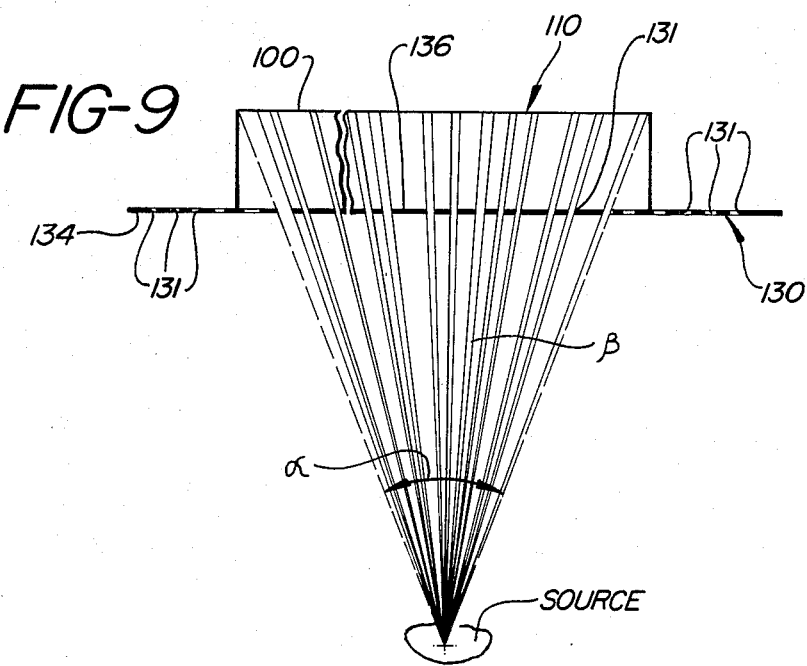

HYBRID COLLIMATOR

TECHNICAL FIELD

This invention relates to a collimator for a gamma or scintillation detector and more particularly to a hybrid collimator comprising a multichannel collimator and a coded aperture. The hybrid collimator is intended to obtain images of the radioactive distribution of material in patients using a radioisotope camera from multiple directions for subsequent mathematic reconstruction of the tomographic distribution of radioactive materials. The hybrid collimator is a substitute for the parallel hole or pinhole collimator conventionally used on a radioisotope camera.

BACKGROUND ART

Images of the distribution of radioactive materials in patients is customarily performed with radioisotope cameras as parallel ray projections. The collimation of the gamma rays emitted by the radioactive materials is provided by the radioisotope camera through parallel hole collimators or pinhole collimators. Additional information concerning the depth distribution of radioactive material, i.e., tomographic information, may be obtained by imaging with a radioisotope camera from multiple directions and mathematically estimating the tomographic distribution of radioactive materials.

Multiple projection information for tomographic imaging can be obtained by rotating camera systems, circular multidetector array systems, or stationary camera limited-viewing-angle-tomography systems. Rotating camera systems and reconstruction software are available in the commercial market. Multi-detector circular arrays are most commonly used for positron emission imaging and such systems are available commercially. Rotating camera systems require hardware, not normally found in conventional systems, which adds significantly to the cost of a radioisotope camera and may interfere with the normal use of the camera. Circular multidetector arrays are generally too expensive and are not suitable for conventional planar imaging.

Limited viewing angle tomography systems which can be implemented on a stationary radioisotope camera have been of interest because of the low cost associated with this approach. Two approaches are in common use and are commercially available; an array of 7 pinholes which generates separate images in a seven segment field of a radioisotope camera is described by Vogel, et al., "A New Method of Multiplanar Emission Tomography Using a Seven Pinhole Collimator and a Anger Scintillation Camera", J. Nucl. Med. 19:648–654, 1978 and a rotating slant hole collimator system which collects multiple views by rotating the collimator system as taught in U.S. Pat. No. 4,302,675 to Wake, et al. Both approaches provide projection information in only a limited number of directions.

Three other approaches have been described in the literature but have not been implemented commercially; the stationary non-redundant coded aperture, the fourier multi-aperture collimator and the time modulated coded aperture.

Stationary-coded techniques are attractive because of their potential for dynamic cardiac studies. However, reconstructions are subject to structured noise reflecting the cross correlation pattern of the code, and it is not possible to uniquely identify individual radiation ray paths and thus apply attenuation corrections. The inability to provide for attenuation corrections is a serious disadvantage.

The fourier multi-aperture method has short computation times associated with the coding of the tomographic information because of the applicability of fast fourier transform algorithms. However, because the information is collected in the frequency domain there does not appear to be a satisfactory approach to attenuation correction.

Pseudo random coded aperture imaging introduces the variable of time into a code pattern. By correlating the observed data with the known, time variant, characteristic of the collimator it is possible to reduce the data collected to a set of pinhole images. As such, the preprocessed data represents direct ray sums which can be reconstructed using conventional methods and attenuation corrections may be applied. The general method for time-modulated pseudorandoom coded aperture imaging is described by Koral K. F., Rogers W. L., and Knoll A. F., "Digital Tomographic Imaging with Time-Modulated Pseudorandom Coded Aperture and Anger Camera", The University of Michigan, J. Nucl. Med. 16:402–413, 1975 (hereinafter "Koral"). The disadvantage of the time modulated coded aperture method is the large reconstruction time that is noted in the University of Michigan study. In order to keep the reconstruction tractable, it is necessary to use a limited number of apertures (essentially pinhole apertures). The effect of the reduced number of apertures is to limit the information sampling in the frequency domain.

SUMMARY OF THE INVENTION

This invention is a new approach to stationary radioisotope camera limited viewing angle tomography. The invention comprises a special purpose collimator intended for use with a conventional radioisotope camera. Multiple planes at different heights within the body are decoupled by parallel plates. The use of parallel plates is analogous to the use of parallel holes in conventional collimators. The parallel plates block the oblique radiation rays and reduce the data collection rate. The collimation of rays in the orthogonal direction is provided by closely spaced pseudo random time modulated apertures. The invention provides for projection ray sampling which is finely spaced in both the angular and spatial directions. The use of coded aperture collimation provides for an improvement in the image signal-to-noise ratio for areas of high radioactivity when compared with conventional imaging based on the same number of counts collected. The individual aperture holes can be synchronously controlled in the multiple rows defined by the parallel plates. Thus a large number of apertures (such as $64 \times 73 = 4,672$) may be controlled by a few number of actuators (73). This is a notable improvement over the approach described by Koral and is essential to the fine sampling provided by this invention. The data collected using this hybrid collimator is mathematically reduced to a set of parallel ray projections at multiple angular directions. This is an advantage not provided by any other limited angle tomography approach. The information in this form has potential applicability for diagnosis as a pseudo holographic display. Furthermore, the information can be reconstructed by utilizing conventional parallel ray back projection techniques with attenuation correction. Since the information in different rows corresponding to the separation between parallel plates is decoupled, the mathematic reconstruction reduces to a set of independent reconstructions.

BRIEF DESCRIPTION OF THE DRAWINGS

FIG. 6 is a section of the multi-channel collimator taken along line 6—6 of FIG. 5;

FIG. 7 is a geometric illustration showing a fan beam $\alpha$ as limited by the length of a channel of the multi-channel collimator;

FIG. 8 is a section taken along 7—7 of FIG. 6 geometrically illustrating the thickness $\theta$ of fan beam $\alpha$ as defined by a pair of adjacent plates of the multi-channel collimator;

FIG. 9 is a geometric illustration showing the ray portions of fan beam $\alpha$ which are transmitted to the detector by apertures in the code plate in a stationary position;

BEST MODE FOR CARRYING OUT THE INVENTION

Figure 1:
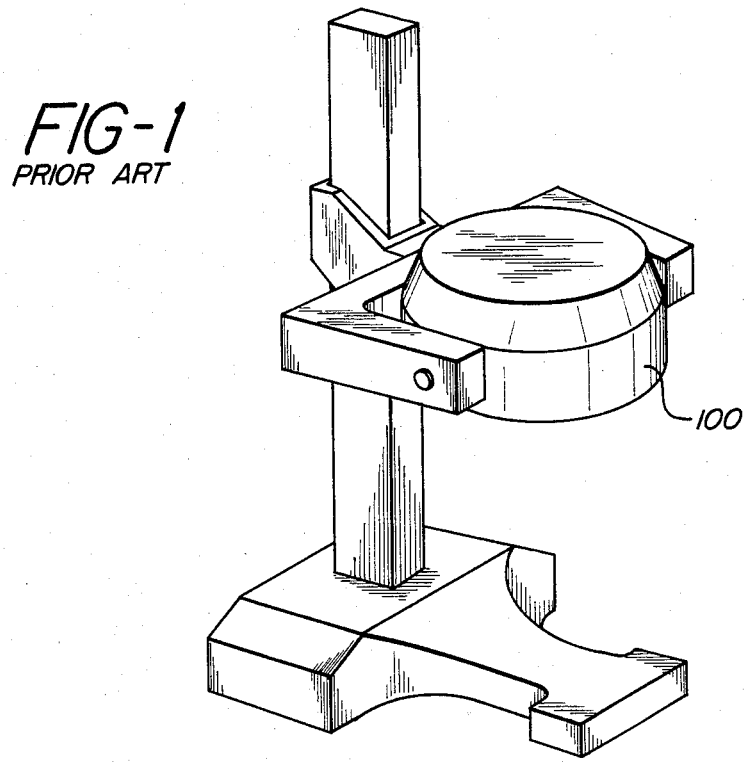
FIG. 1 illustrates a stand for a nuclear camera with a detector head positioned thereon.
Figure 5:
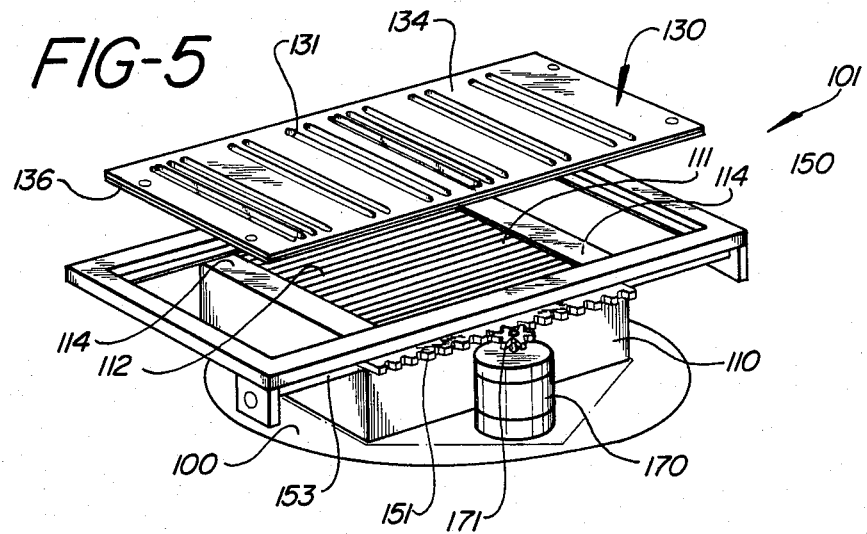
FIG. 5 is an exploded view in perspective of the hybrid collimator according to the invention.

Referring first to FIG. 5, there is shown the hybrid collimator concept referred to generally as 101. The hybrid collimator includes a multi-channel collimator 110, a coded aperture plate 130, frame member 150, and stepping motor 170, each of which will be described in greater detail below. The hybrid collimator 101 is adaptable for use with virtually any conventional nuclear imaging device, but will be described herein specifically as adapted for mounting on a Technicare Corporation Model 438 wide field gamma camera, shown in FIG. 1. The physical dimensions provided herein reflect the usable field of view for that camera which is hexagonal with a 14.5 inch inscribed circle.

The multi-channel collimator 110 includes 64 identically dimensioned parallel channels 111, each 380 millimeters long, 130 millimeters deep, and 3 millimeters wide. The channels 111 are separated by 0.5 millimeter wide molybdenum plates 112 so that the overall width of the collimator 110 is 225 millimeters ($\approx 64 \times 3.5$ mm). The multi-channel collimator 110 is arranged so that alternate plates 112 are removable, thereby creating a 32 channel collimator with each channel 6.5 millimeters wide. A radiopaque mask 114, as shown in FIG. 6, is provided at either end of the multi-channel collimator 110. The masks 114 are preferably lead or tungsten plates approximately 2 millimeters thick. The channels 112 are enclosed by L-shaped radiopaque side walls 115 fabricated of lead with a thin strip 116 of steel or aluminum.

Molybdenum is the preferred material for plates 112. Molybdenum makes for simplified fabrication and ease of removal when it is desired to alter the number of channels. In addition, molybdenum is advantageous since it retains a highly precise geometry. Alternatively, a thin lead foil may be utilized to separate adjacent channels. Both materials provide sufficient attenuation to accomplish the necessary collimation for imaging with technetium as well as thallium. Less desirable materials would be a copper/bronze alloy, iron, tungsten, tantalum, or virtually any high atomic number, high density material. The separation between adjacent plates need not be air gaps but may be provided by low density foamed plastic, provided that the attenuation of gamma rays by the plastic foam is relatively small, i.e., no more than 5%. Such low density foam spacers would be required if channel separation were to be provided by lead foil. Regardless of the materials used in the fabrication, the field of view of each image after time decorrelation and ray reordering is 225 millimeters $\times$ 255 millimeters.

The available field of view may be altered by making the plates 112 nonparallel. For instance, if the plates converged toward the patient, the field of view would be reduced, with an attendant increase in resolution and sensitivity. Correspondingly, if the plates diverged relative to the patient, a larger field of view would be imaged, with a corresponding loss in resolution and sensitivity.

Figure 3:
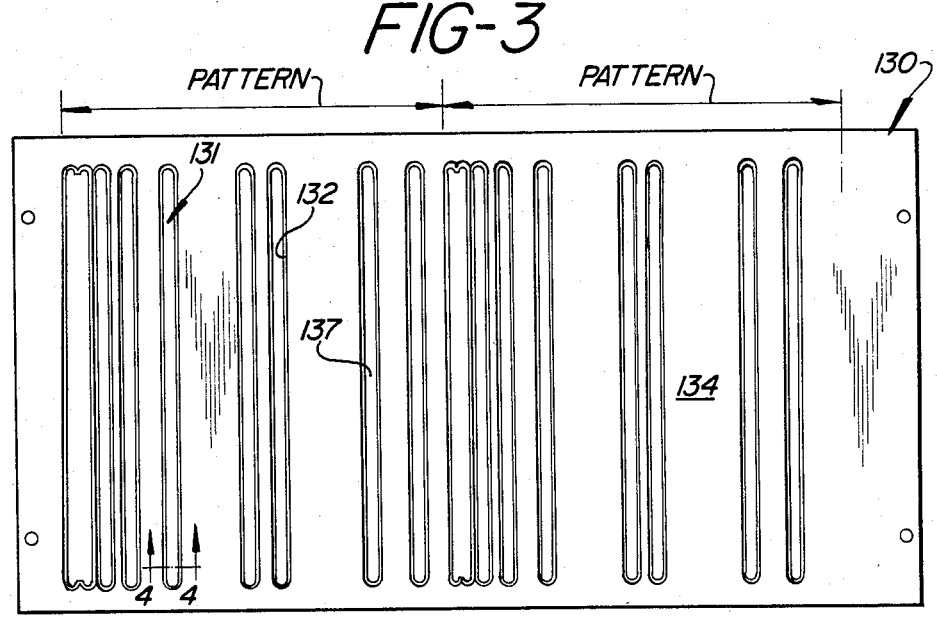
FIG. 3 illustrates a coded aperture plate in greater detail than that shown in FIG. 2 illustrating an array of parallel splits arranged thereon.
Figure 4:
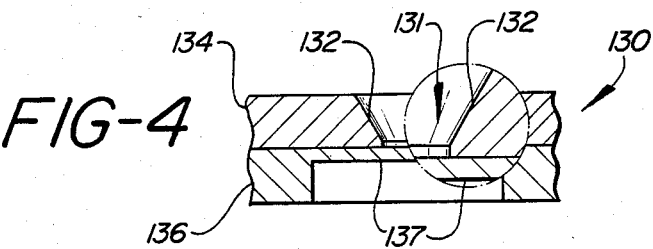
FIG. 4 is a section taken along line 4—4 of FIG. 3.

With the coded aperture plate 130 removed, and hence no coding, the entire space of each channel 111 is able to transmit radiation from an external point to a gamma or scintillation detector 100. To code the multi-channel collimator 110, that is, to render some portions of at least some of the channels 111 non-transmissive, an aperture plate such as 130 is used. Coded aperture 130, an embodiment of which is illustrated on a enlarged scale in FIG. 3, is a flat, laminated, rectangular code plate with radiotransparent slits 131 arranged in a pseudorandom sequence or pattern replicated twice. The code plate is approximately 520 millimeters long and 225 millimeters wide, so as to cover the entire width of the multi-channel collimator 110. As is shown in the cross section of a single radiotransparent slit 131 in FIG. 4, the coded plate 130 is laminate fabrication consisting of a lead plate 134 bonded to an aluminum frame 136. Since a relatively thin strip of aluminum such as at 137 is acceptably radiotransparent, the opening for slit 131 need not extend through the entire bonded configuration of plate 130. This fabrication technique permits the plate 130 and, in particular, the walls 132 of slit 131 to be very thin while at the same time affording the requisite precision to the opening of each aperture 200 and providing a sturdy construction. The bevelled edge or wall 132 of either side of slit 131 permits greater precision in fabricating each slit to the desirable width of 2.7929 millimeters. The code plate 130 employs a 73 element code, with a mean transmission of about 12%, the open fraction ratio (9 openings/73 positions).

Figure 2:
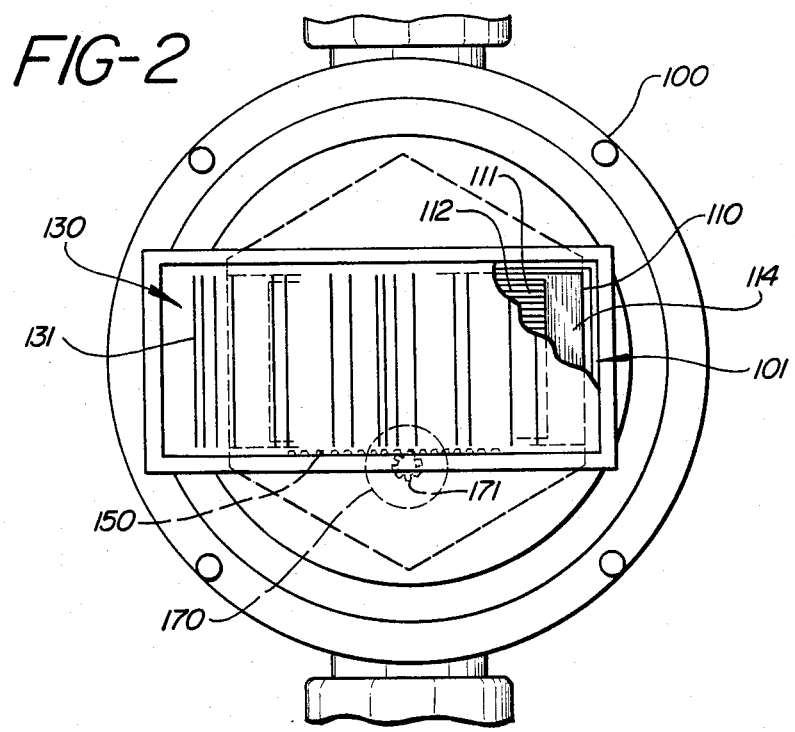
FIG. 2 illustrates a plan view of the face of a scintillation detector with hybrid collimator according to the invention positioned thereon.

Each radio transparent slit 131 extends over a substantial portion of the width of code plate 130 such that when the code plate is aligned atop the multi-channel collimator 110 as shown in FIG. 2, the code is identical for each channel 111. Thus, the aperture pattern for each channel 111 is identical to all other channels.

It is not essential that there be 73 elements in the code, nor is it essential that this particular code pattern be utilized. The 73 element code employed in the best mode was selected on the basis of two considerations. The 73 elements combined with the overall geometry of the collimator provides for an opening of approximately 2.8 millimeters. The separation between the two end plates 114 is 203.88 millimeters (73×2.7928 mm). This slit width is a desirable size in that it matches the pixel size of an Anger camera image when digitized with 128 elements. Codes with fewer elements provide aperture widths larger than desirable whereas codes with a greater number of elements will provide apertures narrower than can be handled conveniently. The number of code elements which are open in the pseudorandum pattern illustrated in FIG. 3 provides for a 12% open ratio resulting in acceptable signal to noise ratios in cardiac studies.

The code plate 130 is disposed atop the multi-channel collimator 110 in a frame 150 provided therefor. The detector-to-plate distance is 130 millimeters, a distance selected with cardiac-thoracic anatomy in mind. A 30 degree acceptance cone is required to cover the myocardium. The 130 millimeters distance assures that a straight line extending from the juncture 117 between a side wall 115 and the detector 100 and the inner edge 118 of corresponding end plate 114 is at a 30° angle relative to the normal portion of said side wall. The 130 millimeter distance allows the code plate 130 to be as close to the patient as possible while still permitting the myocardium to fit within the 30 degree cone. The close proximity of the plate 130 to the patient provides both a high degree of sensitivity and superior resolution.

The time dependent nature of the code is provided by a mechanism which advances the code plate 130 in frame 150 in a direction parallel to the lengthwise orientation of each plate 112 of the multi-channel collimator 110. Thus, discrete linear portions of each channel 111 block and transmit radiation in a time dependent fashion as defined by the pattern of the code plate 130. Since the lateral slits 131 of code plate 130 are all parallel and extend laterally relative to the lengthwise or longitudinal direction of the multi-channel collimator, the open/closed pattern will be the same for each channel 111.

A stepping motor 170 is used to advance the aperture plate 130 across the collimator channels 111. A stepping motor drive with a computer interface, described in detail below in connection with FIG. 11, allows the computer performing the image data collection to control the motion of the stepping motor through an RS232 computer interface. The stepping motor 170 provides increments of motion of approximately 0.2 millimeters with extreme precision. The stepping motor 170 includes a drive gear 171 whose teeth are designed to engage rack 151 thereby advancing frame 150 with code plate 130 secured therein either to the right or left, as desired, by means of guide rod 153. Alternatives to the stepping motor 170/drive gear 171/rack 151 mechanism include any form of linear actuator such as a linear stepping motor, a linear solenoid and ratchet mechanism or a servomotor with linear position feedback.

In a conventional parallel hole collimator, the collimator allows only those gamma rays travelling in a direction essentially parallel to the axis of its holes to pass through to the detector. Thus, for a point source of photon emission, gamma rays are emitted in any of $4\pi$ steradians, but only a very small percentage of those emissions, those that are emitted within a small solid angle, will be detected. In contrast, the multi-channel collimator 110 of the present invention with the code plate 130 removed, transmits all gamma rays from a point source travelling within a fan angle $\alpha$ of some finite thickness $\theta$. The angle $\alpha$, as illustrated in FIG. 7, is determined by the length of the channel 111 and the distance between the emitting source and the detector 110, while the thickness $\theta$, as illustrated in FIG. 8, is determined by the spacing between adjacent plates 112 as well as the source-detector distance. Thus, the cross section of the fan varies from a point at the source to the cross sectional dimension of the channel 111 at detector 110.

As shown in FIG. 9, with code plate 130 in place, the transmissive portion of each channel 111 is significantly reduced by the radiopaque portion 134 of the code plate. That is, only those portions of each channel 111 over which a slit 131 lies will transmit radiation. Since the slits 131 are oriented in a direction orthogonal to the lengthwise direction of each channel 111 and since they overlap the entire array of channels, the open/closed pattern over each channel is identical to all others.

Figure 10:
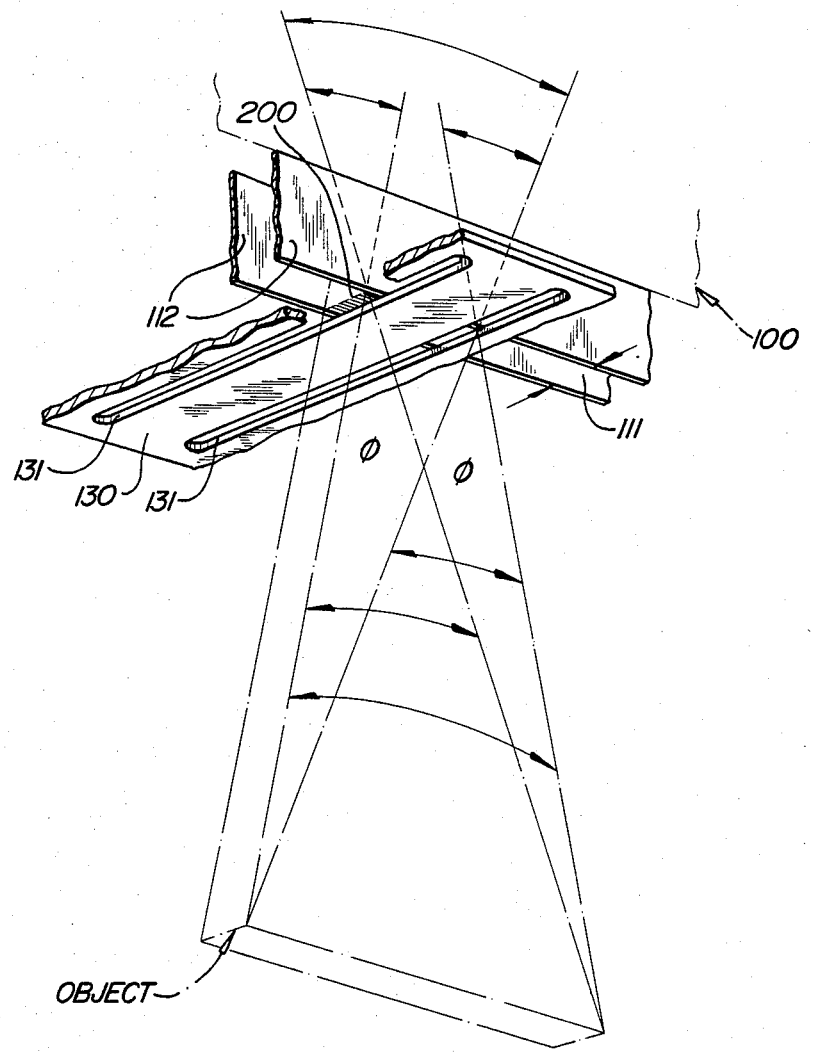
FIG. 10 is a geometric illustration showing the fan beam $\phi$ received by an aperture of a slit of the code plate.

The code plate can be conceptually understood as a series of adjacent slits (73 in the current implementation)—each of which at any particular time may be opaque or transmissive—which collect data autonomously. Each slit in combination with adjacent pairs of parallel plates 112 forms an aperture 200 (as shown in FIG. 10). Since the parallel plates 112 of the multi-channel collimator 110 constrict gamma rays permitted to pass therethrough to the detector to a fan beam of thickness $\theta$, each aperture 200 can measure a multiple point source such as that shown in FIG. 10 as defined by angle $\phi$. Since the aperture 200 is repeated 64 times (one for each channel 112) for each slit, there are 64 measurements in 64 parallel planes collected simultaneously which are combined to form an image of the entire object. Inherent in the concept is the ability to collect data from multiple slits (i.e. multiple fan beams) simultaneously. The ability to collect data simultaneously and still associate the data with specific slits is accomplished by opening and closing each slit with a characteristic time pattern. The time modulation property makes the concept a time coded aperture.

The time code employed alternately opens and closes a particular slit. Adjacent slits differ by having their time pattern delayed by one element. This property allows the time pattern to be implemented by sliding a coded plate over the adjacent aperture positions. The time varying pattern is established as a spatial pattern on the moving plate.

The time pattern employed is a pseudorandom time sequence. The sequence can be described by a series of elements having values of zero or one. A zero is interpreted as a closed (opaque) aperture and a one as an open (transmissive) aperture. A class of time sequences exists such that the autocorrelation of the time sequence produces a high value when the sequence is aligned on itself and low constant values when the pattern is a shifted to misaligned positions. The code employed (i.e. the pattern of slits) need not be the one illustrated in FIG. 3). In general, the code plate between the parallel plate collimator and the patient could represent virtually any pseudo-random code.

Moreover, the code plate may be made time modulated in a variety of ways other than described hereinabove. For example, a code plate could consist of many (50–200) individual shutters, each 2–6 mm wide and roughly 225 mm long. With an individual actuator per shutter, any pseudorandum pattern could be implemented. The shutters could be mechanical in operation, inserting or withdrawing radiopaque material; or could be hydraulic in nature, filling a tube with either air or a dense liquid such as mercury. The shutters would provide the code plate with a time-modulation without the need to physically advance the code plate across the collimator.

Figure 11:
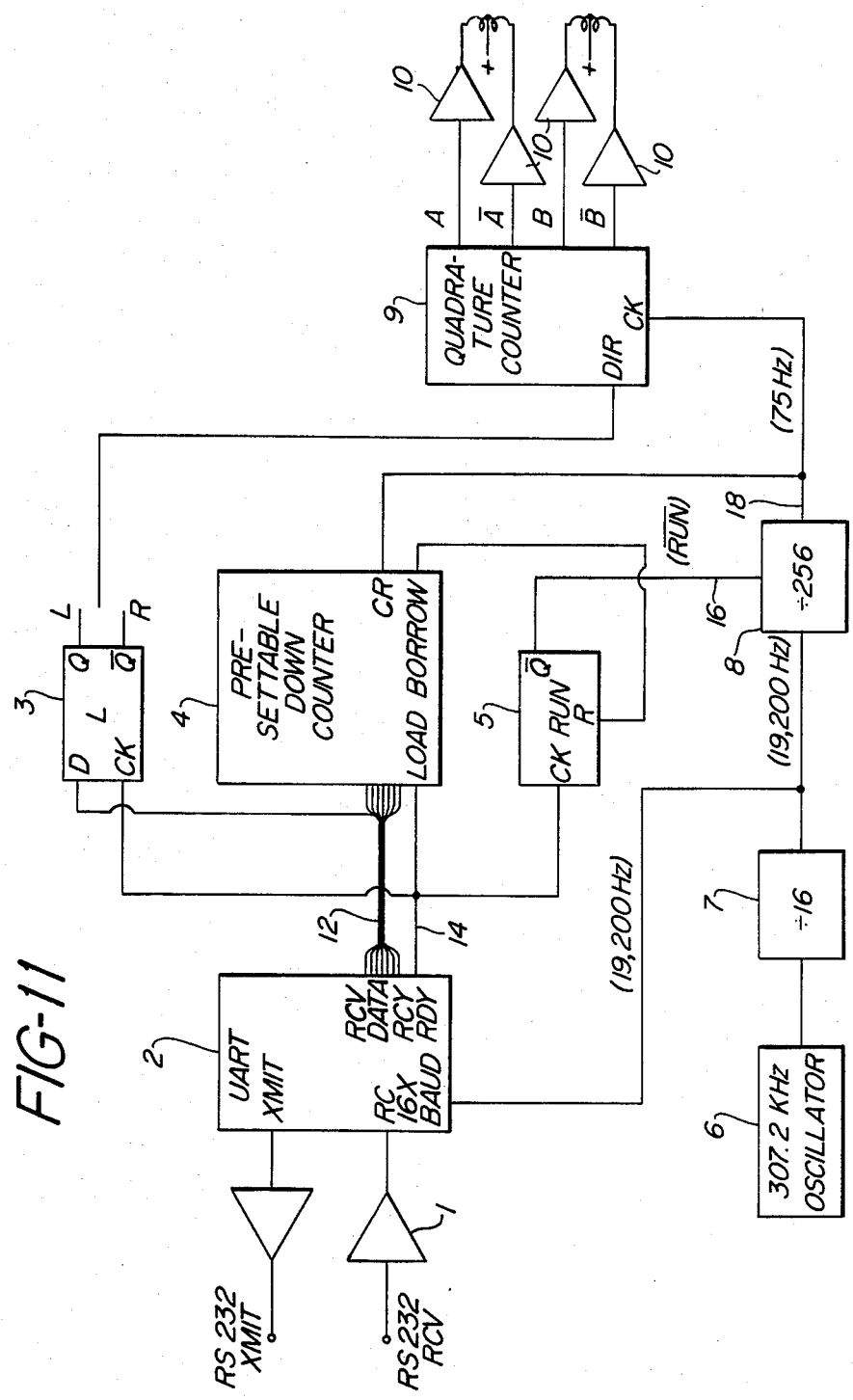
FIG. 11 is a functional block diagram illustrating interface electronics used in advancing the coded aperture relative to the multi-channel collimator across the face of the scintillation detector.

An example of interface electronics for implementing the movement of the code plate 130 across the collimator channels is shown in FIG. 11. The interface electronics between the hybrid collimator 101 and a computer (not shown) permits the computer to move the code plate 130 in either direction (left or right) up to 64 steps via the transmission of an American Standard Code for Information Interchange (ASCII) character over an RS232 serial line, at a data transmission rate of 1200 bits per second (baud).

The RS232 translator 1 converts RS232 levels (±14 volts) to TTL levels (0, +5 volts). A universal asynchronous receiver transmitter (UART) 2 receives a serial character and converts it to a parallel word on the RCV DATA lines 12. The least significant 6 bits of this word represents one less than the number of steps to move and the 7th or most significant bit (MSB) represents the direction to move. For example, a binary "1" as the MSB represents movement to the left and a binary "0" represents movement to the right.

When the character is received by the UART 2, the RCV RDY line 14 pulses, loading the directional bit into a latch 3, the size of the step less one into a Presettable 6-bit Down Counter 4 and sets a RUN latch 5 to its Run state.

A 307.2 KHz oscillator 6 is divided down to 19.2 KHz by a ÷16 binary counter 7. The 19.2 KHz output of counter 7 is applied to the 16× BAUD input of the UART thereby establishing the serial line baud rate of 1200 Hz (19,200÷16). When RUN is set false, the $\overline{\text{RUN}}$ line 16 from the RUN Latch 5 holds ÷256 binary counter 8 reset. When RUN is set true, $\overline{\text{RUN}}$ goes low and releases the ÷256 counter 8, which causes the 75 Hz line 18 to start pulsing at 75 Hz (19,200÷256). The 75 Hz line counts down the Presettable 6-Bit Down Counter 4 to zero, at which time the Borrow pulses, resetting the RUN latch. Since the Borrow occurs at 0, there is one more pulse on the 75 Hz line than the number loaded into the Presettable Down Counter from the UART. For example, an exclamation point (!) in ASCII in a binary 0100001 or a decimal 33. If an "!" is transmitted by the computer, the stepping motor makes 34 steps to the right (MSB=0). Transmitting a binary 1100001 or a decimal 97 results in a movement of 34 steps to the left.

The left or right directional indicator from latch 3 is applied to the direction input of a Quadrature Counter 9. The number of steps to be performed in the chosen direction is determined by the number of pulses applied to the Quadrature Counter on the 75 Hz line 18. The Quadrature Counter 9 is a 2 bit counter which counts in Gray code or quadrature. The Counter 9 has two outputs with which to energize the stepping motor 170. Since the A and the $\overline{\text{A}}$ line are complementary as are the B and $\overline{\text{B}}$ line, when the A line is high, the $\overline{\text{A}}$ line (its complement) is low and vice versa. The same applies to the B and the $\overline{\text{B}}$ line. Each output pair represents one step. To count a sequence of steps to the left, the Quadrature Counter 9 would count:

AB, $\overline{\text{A}}$B, $\overline{\text{A}}\overline{\text{B}}$, A$\overline{\text{B}}$, AB, etc.

Conversely, a sequence to the Right is designated:

AB, A$\overline{\text{B}}$, $\overline{\text{A}}\overline{\text{B}}$, $\overline{\text{A}}$B, AB, etc.

As can be seen, Right is the same as Left in reverse order, and vice versa.

The outputs of the Quadrature Counter control Power Drivers 10, which are NPN Darlington power transistors, by sinking current through the windings of Stepping Motor 170. Only one-half of each winding will be energized at one time. The quadrature nature of the Quadrature Counter 9 causes the Stepping Motor 170 to make a 1/200 revolution (1.8°) per step, or per 75 Hz clock. The gear 171 on the stepping motor shaft is a 24 tooth, 48 Diametral Pitch gear, such that 1 step corresponds to 0.19949 mm travel of the code plate 130, and 14 steps corresponds to 2.7929 mm, which is the aperture spacing and which also corresponds to transmitting a carriage return in ASCII.

In operation, the number of steps per move and its direction is programmed as is the length of time between moves. During the idle times, the gamma rays emitted by the radionuclide are detected. The relative position of the code plate 130 is also noted during each data acquisition time period to evaluate subsequent reconstruction of the timed coded data.

I claim:
1. A hybrid collimator for a gamma ray imaging detector of the type having a planar face adapted for positioning adjacent a portion of an object being studied, said hybrid collimator comprising:
   (a) a radiopaque code plate having a prescribed pattern of radiotransparent apertures representing a pseudorandom code sequence in the form of uniform lateral apertures arranged in parallel for the passage of radiation therethrough, said plate oriented generally parallel to the face of the detector and disposed in front of said detector;
   (b) a multi-channel collimator having a multiplicity of spaced apart plates, adjacent pairs of which define an opening for the passage of radiation therethrough, the separation between said adjacent pair of said plates defining the thickness of the opening, with the lengthwise orientation of said openings being orthogonal to the orientation of the apertures of said code plate, said multi-channel collimator disposed between said detector and said plate; and
   (c) means for advancing said plate relative to said collimator across the face of the detector in a direction parallel to the lengthwise orientation of the openings in said multi-channel collimator so that the portion of said collimator permitted to transmit radiation to said detector is time dependent, whereby images of the distribution of radiation emanating from a plurality of planes passing through the object being studied is reconstructed.

2. The hybrid collimator according to claim 1 wherein said code plate includes a 73 element code.

3. The hybrid collimator according to claim 1 wherein said plates of said multi-channel collimator are parallel to one another.

4. The hybrid collimator according to claim 1 wherein said plates of said multi-channel collimator converge toward the detector.

5. The hybrid collimator according to claim 1 wherein said plates of said multi-channel collimator diverge toward the detector.

* * * * *